US009668665B2

(12) United States Patent
Schroeder et al.

(10) Patent No.: US 9,668,665 B2
(45) Date of Patent: Jun. 6, 2017

(54) METHODS AND IMPLANTABLE DEVICES FOR DETECTING ARRHYTHMIA

(71) Applicant: CAMERON HEALTH, INC., St. Paul, MN (US)

(72) Inventors: Mark R. Schroeder, San Clemente, CA (US); Venugopal Allavatam, Maple Grove, MN (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

(21) Appl. No.: 14/815,660

(22) Filed: Jul. 31, 2015

(65) Prior Publication Data
US 2016/0045130 A1  Feb. 18, 2016

Related U.S. Application Data

(60) Provisional application No. 62/036,916, filed on Aug. 13, 2014.

(51) Int. Cl.
| *A61B 5/04* | (2006.01) |
| *A61B 5/00* | (2006.01) |
| *A61B 5/0452* | (2006.01) |
| *A61N 1/39* | (2006.01) |
| *A61N 1/362* | (2006.01) |
| *A61N 1/37* | (2006.01) |

(52) U.S. Cl.
CPC ........ *A61B 5/04012* (2013.01); *A61B 5/0452* (2013.01); *A61B 5/686* (2013.01); *A61N 1/3622* (2013.01); *A61N 1/3702* (2013.01); *A61N 1/3925* (2013.01); *A61N 1/3956* (2013.01)

(58) Field of Classification Search
CPC .................................................... A61B 5/0452
See application file for complete search history.

(56) References Cited

U.S. PATENT DOCUMENTS

| 4,453,551 | A | 6/1984 | Anderson et al. |
| 6,505,068 | B2 | 1/2003 | Bonnet et al. |
| 6,556,859 | B1 | 4/2003 | Wohlgemuth et al. |
| 6,647,292 | B1 | 11/2003 | Bardy et al. |
| 6,721,597 | B1 | 4/2004 | Bardy et al. |
| 6,754,528 | B2 | 6/2004 | Bardy et al. |
| 7,149,575 | B2 | 12/2006 | Ostroff et al. |
| 7,194,302 | B2 | 3/2007 | Bardy et al. |
| 7,330,757 | B2 | 2/2008 | Ostroff et al. |
| 7,756,571 | B1 | 7/2010 | Farazi |
| 7,970,473 | B2 | 6/2011 | Nabutovsky et al. |
| 8,005,533 | B1* | 8/2011 | Farazi ................. A61B 5/0452 600/515 |
| 8,055,333 | B2 | 11/2011 | Duann et al. |
| 8,160,686 | B2 | 4/2012 | Allavatam et al. |

(Continued)

*Primary Examiner* — Eric D. Bertram
(74) *Attorney, Agent, or Firm* — Seager, Tufte & Wickhem LLP

(57) ABSTRACT

Methods and devices for accelerating the identification of arrhythmias in implantable medical devices. Following identification of a potential arrhythmia onset condition, such as by identifying a plurality of closely coupled detected events, a retrospective pattern recognition analysis is performed to seek out a possible onset comprising a Torsades de Pointes. Although the methods and devices are designed to target Torsades de Pointes, wider application to other arrhythmia onset conditions is contemplated as well.

20 Claims, 8 Drawing Sheets

(56) References Cited

U.S. PATENT DOCUMENTS

| | | |
|---|---|---|
| 8,160,687 B2 | 4/2012 | Warren et al. |
| 8,160,697 B2 | 4/2012 | Warren et al. |
| 8,265,737 B2 | 9/2012 | Warren et al. |
| 8,521,266 B2 | 8/2013 | Narayan et al. |
| 8,521,276 B2 | 8/2013 | Sweeney et al. |
| 8,565,878 B2 | 10/2013 | Allavatam et al. |
| 8,588,895 B2 | 11/2013 | Sanghera et al. |
| 8,639,316 B2 | 1/2014 | Sarkar |
| 8,700,140 B2 | 4/2014 | Narayan et al. |
| 8,744,555 B2 | 6/2014 | Allavatam et al. |
| 8,838,222 B2 | 9/2014 | Narayan et al. |
| 8,838,223 B2 | 9/2014 | Narayan et al. |
| 8,868,169 B2 | 10/2014 | Narayan et al. |
| 9,089,269 B2 | 7/2015 | Narayan et al. |
| 9,215,987 B2 | 12/2015 | Trayanova et al. |
| 2005/0234363 A1* | 10/2005 | Xue .................. A61B 5/0452 600/515 |
| 2012/0046563 A1 | 2/2012 | Allavatam et al. |

* cited by examiner

METHODS AND IMPLANTABLE DEVICES FOR DETECTING ARRHYTHMIA

CROSS REFERENCE TO RELATED APPLICATIONS

The present application claims the benefit of and priority to U.S. Provisional Application No. 62/036,916, filed on Aug. 13, 2014, the disclosure of which is incorporated herein by reference.

BACKGROUND

Implantable cardiac systems, such as implantable defibrillators, are designed to identify and treat certain cardiac arrhythmias. Arrhythmias are generally identified by the analysis of electrical signals in the patient, though other signals (movement, sounds, etc.) may also be integrated into the analysis. The electrical signals which emanate from the heart during both non-treatable and treatable cardiac activity can vary widely. New and alternative methods for identifying treatable cardiac activity are needed.

OVERVIEW

The present inventors have recognized that certain arrhythmias can be identified by the use of a set of rules and pattern recognition. In particular the rule set is directed toward the positive identification of likely ventricular fibrillation which presents itself with markers for Torsades de Pointes. When the onset of ventricular fibrillation takes a Torsades de Pointes form, a far field detection scheme can have difficulty detecting cycles of the arrhythmia due to the varying amplitude of the cardiac signal. The present subject matter can help provide a solution to this problem, such as by applying a set of pattern recognition rules directed toward possible Torsades de Pointes in response to identification of possible conditions of arrhythmia.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Each of the following non-limiting examples can stand on its own, or can be combined in various permutations or combinations with one or more of the other examples.

As used herein, a signal is sensed by an implantable cardiac device system, events are detected in the sensed signal, and cardiac rhythms are classified by use of the detected events. Detected events may also be referred to as detections. Classification of the cardiac rhythms may be referred to as rhythm analysis. Cardiac rhythm classification can include identification of malignant conditions, such as ventricular fibrillation or certain tachyarrhythmias, for example.

The present invention may be used in implantable monitoring or therapy systems. Implantable therapy systems make therapy/stimulus decisions in reliance upon rhythm classification, while monitoring systems make data recording decisions using rhythm classification, where applicable. Therapy systems may deliver electrical, pharmaceutical or other therapy. Some illustrative implementations of the present invention may be in pacemakers and defibrillators, though other implementations are also envisioned. Any of these systems can, if so configured and enabled, generate annunciating (audible tones or palpable vibrations) or communicating (telemetry) signals in response to rhythm classification, in addition to or as an alternative to therapy. Additional implementations can take the form of implantable monitoring systems, which may use cardiac signal analysis to determine whether data is to be recorded for later retrieval, or to take other actions such as emitting a warning or annunciating data.

Figure 1:
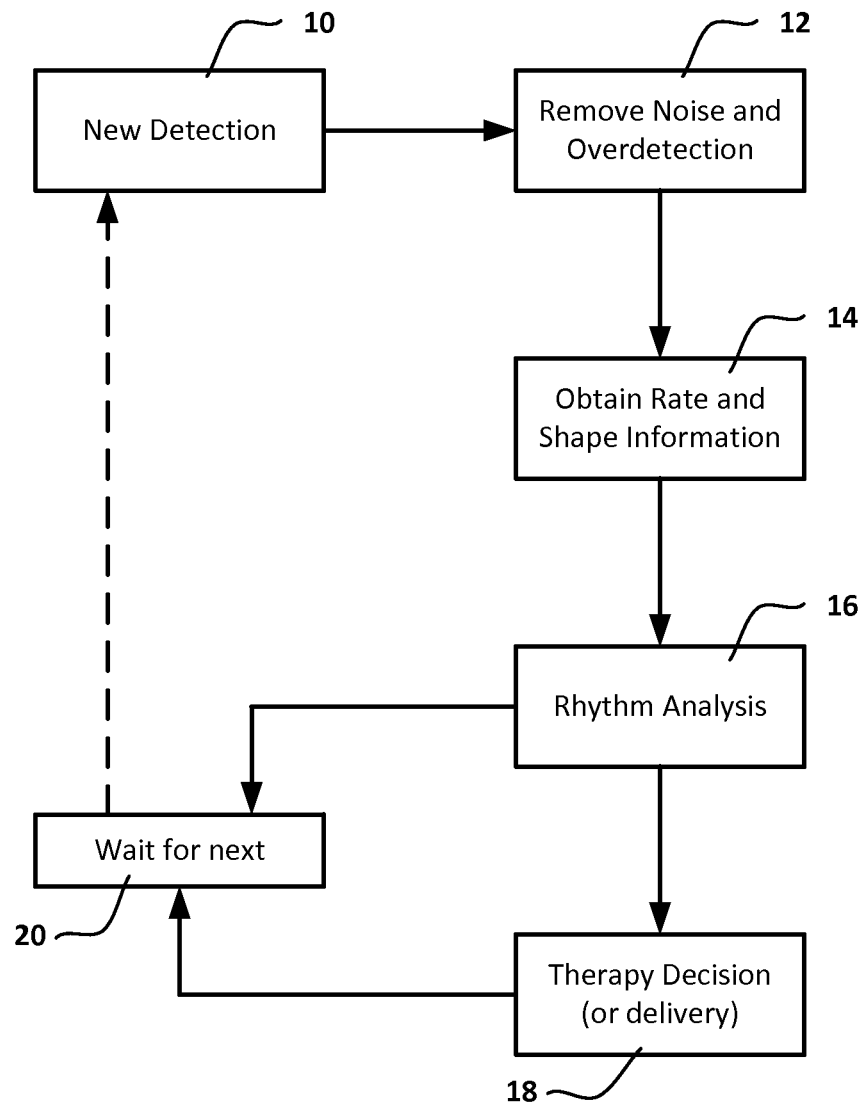
FIG. 1 shows an overall method of cardiac signal analysis including rhythm analysis and therapy decisions.

FIG. 1 shows, in block form, a method of cardiac signal analysis for an implantable medical device. The analysis is cyclic and can be understood as beginning with a new detection or detected event 10. Illustrative detection methods are shown below and may be understood as well from U.S. Pat. No. 8,565,878, titled ACCURATE CARDIAC EVENT DETECTION IN AN IMPLANTABLE CARDIAC STIMULUS DEVICE, the disclosure of which is incorporated herein by reference. Other detection methods may be used instead.

Once a detected event is identified, the analysis then performs assessments to identify noise and/or overdetection as shown at 12. Noise may be identified, for example, as shown in U.S. Pat. No. 8,744,555, titled ADAPTIVE WAVEFORM APPRAISAL IN AN IMPLANTABLE CARDIAC SYSTEM, the disclosure of which is incorporated herein by reference. Overdetection may be identified, for example, as shown in U.S. Pat. Nos. 8,160,686 and 8,160,687, each titled METHODS AND DEVICES FOR ACCURATELY CLASSIFYING CARDIAC ACTIVITY, U.S. Pat. No. 8,265,737, titled METHODS AND DEVICES FOR IDENTIFYING OVERDETECTION OF CARDIAC SIGNALS, and/or US Published Patent Application No. 2012-0046563, titled METHODS AND DEVICES THAT IDENTIFY OVERDETECTION IN IMPLANTABLE CARDIAC SYSTEMS, the disclosures of which are incorporated herein by reference. Other noise identification and/or overdetection identification methods may be used instead to address mal-sensing and enhance the accuracy of counting of cardiac cycles.

Next, the analysis method obtains certain useful data such as rate and shape information, as shown at 14. Rate and shape information may then be used for rhythm analysis 16. If the rhythm analysis at 16 determines that therapy may be needed, a therapy decision can be made, as shown at 18. The analysis then waits for the next new detection, as shown at 20.

Illustrative methods useful in blocks 14, 16 and/or 18 are shown in the above incorporated patents and published patent applications as well as U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR, U.S. Pat. No. 7,330,757, titled METHOD FOR DISCRIMINATING BETWEEN VENTRICULAR AND SUPRAVENTRICULAR ARRHYTHMIAS, US Published Patent Application No. 2010-0331904, titled ADAPTIVE CONFIRMATION OF TREATABLE ARRHYTHMIA IN IMPLANTABLE CARDIAC STIMULUS DEVICES, and U.S. Pat. No. 8,588,895, titled ROBUST RATE CALCULATION IN AN IMPLANTABLE CARDIAC STIMULUS OR MONITORING DEVICE, the disclosures of which are each incorporated herein by reference. In addition to these patents and patent applications, various methods are known in the art from various commercially available implementations.

Figure 2:
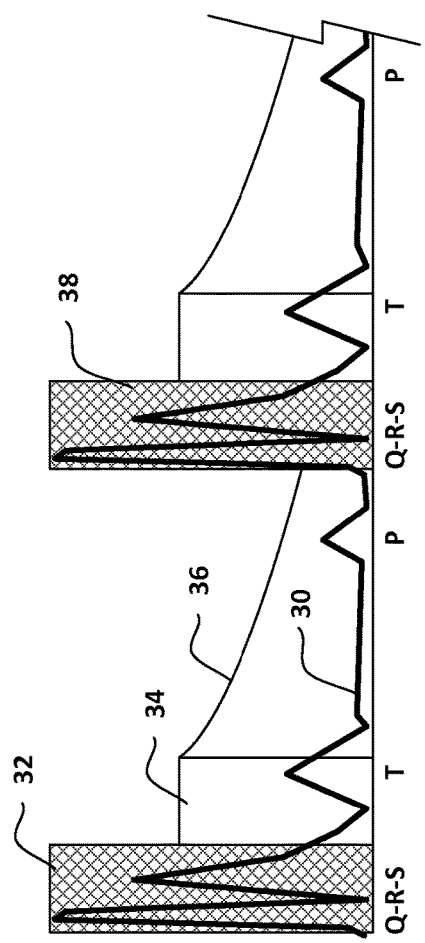
FIGS. 2-3 illustrate the application of a detection threshold to cardiac signals for both normal and treatable high rate cardiac rhythms.
Figure 3:
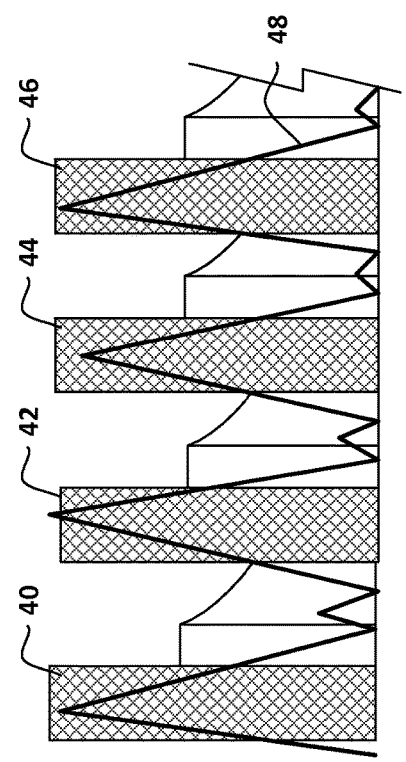

FIGS. 2-3 illustrate the application of a detection threshold to cardiac signals for both normal and treatable high rate cardiac rhythms. A cardiac cycle typically includes several portions (often referenced as "waves") which, according to well-known convention, are labeled with letters including P, Q, R, S, and T, each corresponding to certain physiological events. A normal cardiac cycle usually has all of these parts, though not all may be visible on any given cardiac signal representation. Certain components may not be visible due to factors such as elevated rate, choice of sensing vector, anatomic anomaly, or active arrhythmia, for example. The combination of Q, R and S "waves" can be referred to as the QRS complex. The R-wave and/or QRS complex is often the component of the cardiac cycle that is detected for purposes of identifying a cardiac cycle, since it is typically the largest amplitude component. In some examples, other components may be the target for detection instead, such as the atrial depolarization or P-wave.

In FIG. 2, a cardiac signal is shown at 30, with indications of the Q, R, S, T and P waves shown below. An illustrative detection profile is shown including a refractory period 32, a constant threshold period 34 and a decay period 36. The refractory period 32 defines a time during which the system's operational circuitry will not detect an event, while the constant threshold period and decay period collectively define a time period during which the system's operational circuitry will detect an event if the sensed signal 30 crosses one of lines 34 or 36.

The detection profile 32/34/36 relies in part on the "estimated peak" of the QRS complex. The estimated peak is a measure of amplitude or magnitude, depending on the particulars of a given embodiment, of the cardiac signal being monitored. As the signal grows larger, so too does the estimated peak. In some examples, an estimated peak is the largest peak in a given QRS complex. In other examples, the estimated peak is an average of the largest peaks in the previous two detected cardiac events. Other measures, averages or the like may be used. The estimated peak may be used, for example, by setting the amplitude for the constant threshold period 34 at a percentage of the estimated peak, and/or by setting the beginning point of the decay period 36 to a fraction of the estimated peak.

As shown in FIG. 2, accurate detection of the QRS complex occurs, as the refractory period 32 lasts long enough to cover the entire QRS complex, and the combined constant threshold period 34 and decay period 36 pass over the T-wave and P-wave without an additional detection occurring. That the detection is accurate is observed by noting that there is one refractory period 32, 38, shown in the cross hatching, for each QRS complex.

In the illustrative example shown a refractory period of 200 milliseconds is applied, with the constant threshold period 34 set to an amplitude that is 60% of the R-wave peak amplitude for a duration of 200 milliseconds. The decay period 36 uses a time constant, tau, of 400 milliseconds. The durations, percentages and time constant may all change in other embodiments and those described are merely illustrative. In some examples, the durations, thresholds and/or time constant may be modified depending on the detected rate of cardiac events, or other factors such as whether detected cardiac events correlate to a stored template.

FIG. 3 illustrates detection of a high rate cardiac signal. Here, refractory periods 40, 42, 44, 46 are shown, corresponding to peaks in the cardiac signal 48. It can be seen that there is less detail between the detected peaks in the signal 48, as the predominant signal is itself the individual peaks. This rhythm may be a monomorphic ventricular tachycardia, for example. The detection profile may switch from a slow-rate version to a high-rate version, where the high-rate version of the detection profile uses shorter refractory periods and lower percentages to more aggressively detect the higher rate signal. The detection of the signal in FIG. 3 remains accurate, in part because the amplitudes of the signal peaks are generally similar from one event to the next. Such similarity and resultant accuracy is not always the case, however, as shown in FIGS. 4 and 5.

Figure 4:
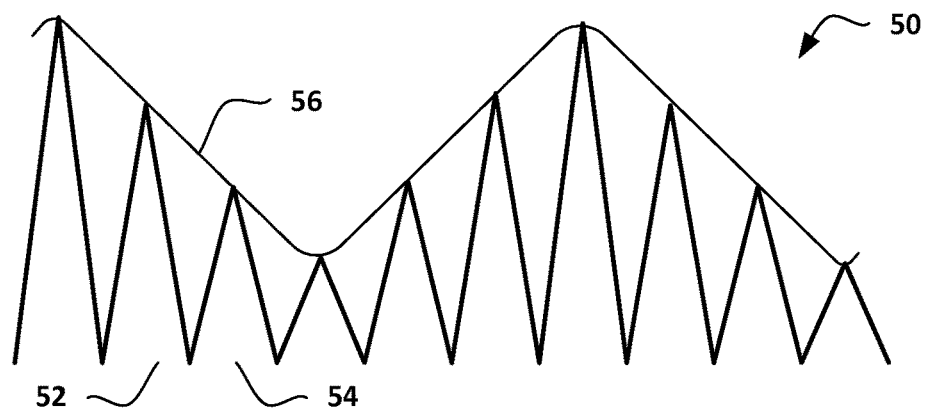
FIG. 4 shows a cardiac signal having a Torsades de Pointes pattern.

FIG. 4 shows a cardiac signal having a Torsades de Pointes (TDP) pattern. TDP is literally translated as "twisting of the spikes", a reference to how observation on a standard ECG will show peaks moving from one side of the baseline to the other over time and, on a multi-lead ECG, will show varying amplitudes across several leads. TDP is a polymorphic ventricular tachyarrhythmia which can cause hemodynamic instability and may degrade into ventricular fibrillation (VF). Many episodes of TDP quickly revert to normal sinus rhythm, but those which do not require therapy.

In some far-field detection vectors of implantable defibrillators, a TDP can be recognized by a pattern as shown in FIG. 4. The signal is shown generally at 50 and includes a series of spikes 52, 54 which demonstrate an undulating overall amplitude tracked by line 56. The signal 50 almost resembles an amplitude modulated radio signal, though with much different frequencies involved, with a relatively slow moving envelope modulating a higher frequency signal. The undulating amplitude 56 can be problematic for cardiac signal detection relying on a detection profile such as that shown in FIGS. 2-3.

Figure 5:
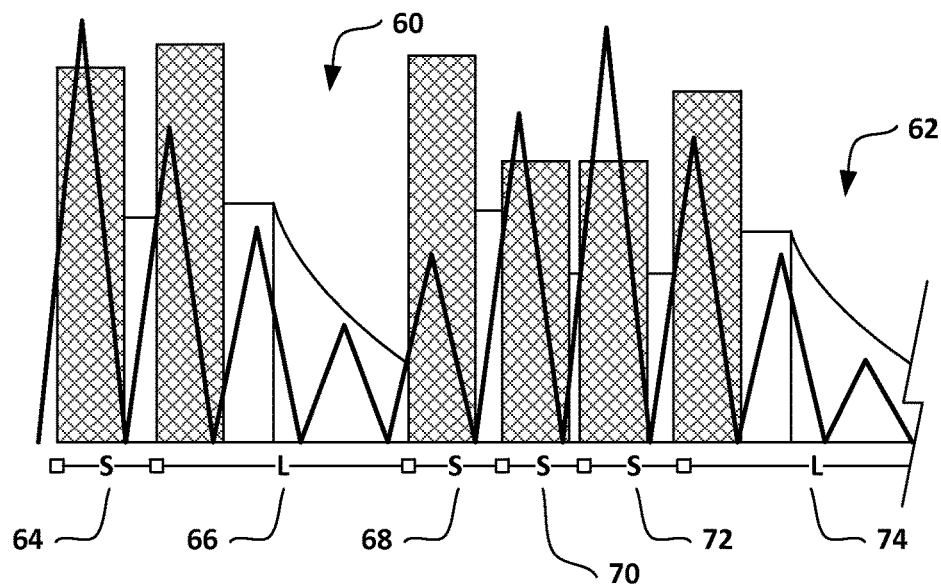
FIG. 5 illustrates delays that can occur when applying a detection threshold to an arrhythmia having a Torsades de Pointes pattern.

For example, FIG. 5 illustrates delays that can occur when applying a detection threshold to an arrhythmia having a TDP pattern at onset. The detections can be identified by the cross-hatched refractory periods, and yield a number of intervals. There are, however, gaps at 60 and 62 in the detection sequences, at times where the event amplitudes are decreasing. The detection profile passes over one or more underlying spikes, as shown at each of 60 and 62. This yields an interval pattern of short interval 64, long interval 66, short intervals 68, 70, 72, and long interval 74. It can be seen that long interval 66 occurs because two consecutive spikes in the signal are missed.

This table puts the sequence in FIG. 5 in numerical terms, with the interval durations provided in milliseconds:

| Interval | 64 | 66 | 68 | 70 | 72 | 74 |
|---|---|---|---|---|---|---|
| Type | Short | Long | Short | Short | Short | Long |
| Duration | 240 | 600 | 225 | 195 | 240 | 600 |

In this numerical example, the true intervals between spikes in the cardiac signal are about 210 milliseconds, which would be about 285 bpm, a rate that most implantable defibrillators would be set to treat as a VF requiring therapy. However, due to the missed spikes in the gaps at 60 and 62, the illustrative system here would calculate an average interval suggesting a rate of about 190 bpm, which may or may not be deemed treatable depending on system parameters.

In addition, most implantable systems require a certain quantity of detected events to indicate an ongoing arrhythmia before determining therapy is needed. Accurate detection of the signal shown in FIG. 5 would identify 10 detected events all falling into a VF rate zone; instead, with the detection as shown in FIG. 5, a system would only find 6 detected events that may or may not fall into a therapy zone. The TDP pattern can, as shown, delay or even inhibit therapy.

As those skilled in the art know, setting arrhythmia declaration parameters more aggressively creates an increased risk of inappropriate therapy, and therefore simply setting a more aggressive therapy regimen is not the preferred solution. As a result, the undersensing shown in FIG. 5 presents a challenge. The present invention, in some embodiments, is directed toward resolving this difficulty.

Figure 6:
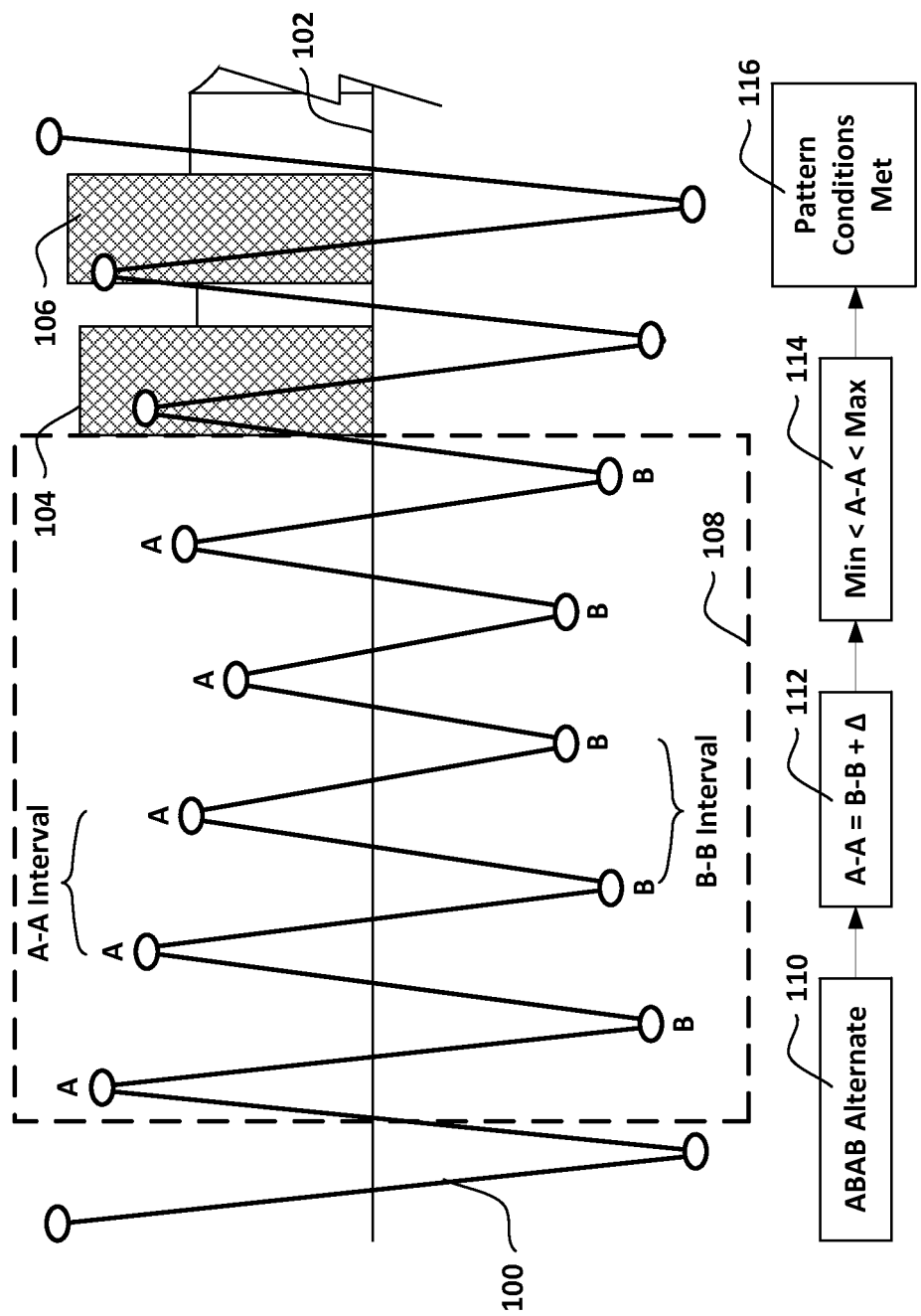
FIG. 6 shows, in graphical form, analysis to identify the arrhythmia pattern causing a delay in FIG. 5.

FIG. 6 shows, in graphical form, analysis to identify the arrhythmia pattern causing a delay in FIG. 5. A signal 100 is shown relative to a baseline 102. The signal, for illustrative purposes, is shown as generally displaying a TDP pattern with an undulating amplitude over time.

The analysis, in this example, can be performed retrospectively upon identification of a trigger. In other examples, the analysis can be performed on a continuous basis. Here, a trigger for performing the analysis is identified with two closely coupled detections shown at 104, 106. The close coupling may be defined, for example, as a beat-to-beat detection interval of less than 300 milliseconds. Other thresholds can be used, with illustrative ranges from 200 to 500 milliseconds. In another example, three closely coupled detections occurring within 600 milliseconds (alternative range of 400 to 1000 milliseconds) may be the trigger. In yet another example, an interval pattern of long-short-short may be used.

Once the (optional) trigger for the analysis is met, a window 108 is set for performing analysis. In this example, the window 108 has a duration of about 1200 milliseconds; other windows with ranges from about 750 milliseconds to about 3000 milliseconds (or longer or shorter) may be used instead.

In this example, the turning points of the signal 100 within the window 108 are then marked ABABAB. In the analysis shown below the window, a first step is to determine whether the turning points alternate about the baseline 102. For this particular example, all the "A" turning points must lie on one side of the baseline 102, while all of the "B" turning points must lie on the other side of the baseline 102. As can be seen, this condition is met as shown at 110.

Next, intervals A-A and B-B are calculated. The A-A intervals may be compared to the B-B intervals, as shown at 112. If the A-A intervals are similar to the B-B intervals (within a boundary condition shown as "delta" in the figure), then block 112 is passed. In some examples, the average of the A-A intervals is compared to the average of the B-B intervals. In some examples, the maximum A-A interval is compared to the minimum B-B interval, as well as the minimum B-B interval being compared to the maximum A-A interval. Thus block 112 may take one of several forms. In the illustration shown in FIG. 6, the condition stated in block 112 is met.

In some examples, and not shown in FIG. 6, the set of A-A intervals are checked to ensure similarity of all A-A intervals with one another. Likewise the B-B intervals may be checked. This step would check that a regular pattern, which is typically discerned with a TDP pattern, is in fact taking place.

Finally, the A-A intervals are checked to ensure that they fall within a predetermined set of boundaries, as shown at 114. The boundaries, MIN and MAX, may be set to ensure that the turning points are not resulting from noise (external or lead-fracture-related, for example) using the MIN limit, and not resulting from a non-treatable condition (a slow rate, for example) using the MAX limit. For example, the MIN limit may be 180 milliseconds (range of about 100 milliseconds to 220 milliseconds), and the MAX limit may be 500 milliseconds (range of about 400 milliseconds to 600 milliseconds).

Again, in the example of FIG. 6, the condition stated in block 114 is met. As a result of meeting the conditions stated in each of blocks 110, 112, and 114, the pattern conditions are met, as shown at 116. Once pattern conditions are met at 116, additional steps may be taken by the implantable device. In several embodiments, an acceleration condition is triggered to cause the device to reach a declaration of treatable arrhythmia immediately or more quickly than would otherwise be the case. In some examples, an acceleration condition may affect the manner in which detected events are sensed, for example applying a shorter refractory period or lower amplitude thresholds for sensing.

Blocks 110, 112 and 114 may be performed in any suitable order. In some examples, one of blocks 112 or 114 may be omitted or substituted with the alternate condition noted above.

Figure 7:
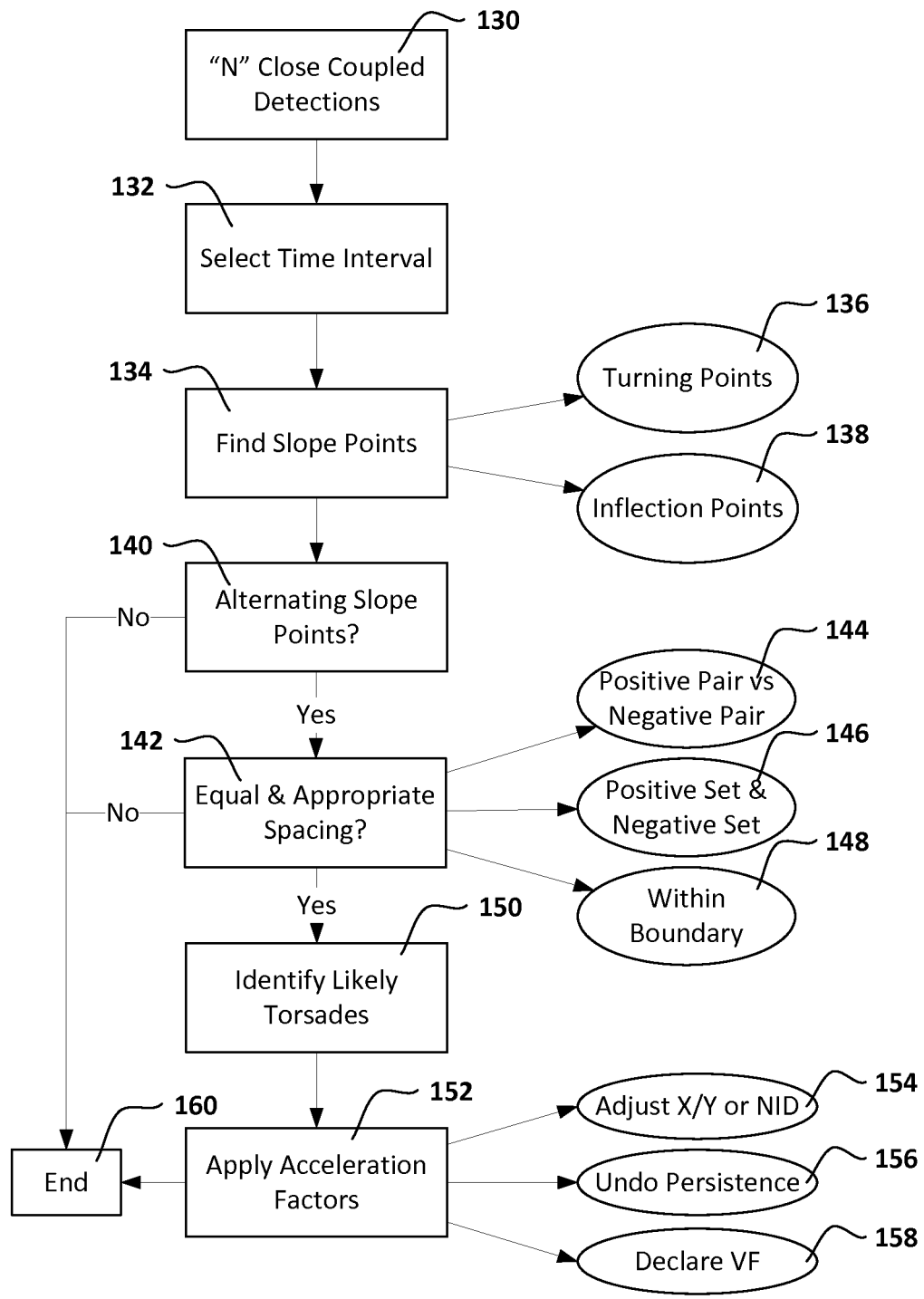
FIG. 7 illustrates the analysis of FIG. 6 in a block form.

FIG. 7 illustrates the analysis of FIG. 6 in a block form. The analysis begins, optionally, with the identification of a triggering condition at block 130. In the example, the trigger is a set of "N" closely coupled detections, where N may be 2, 3 or more detections. Close coupling may be set as desired; in an example, two detections occurring with an interval of less than 300 milliseconds are considered closely coupled. In other example, an interval pattern of Long-Short-Short may be used in block 130. As noted, the analysis may instead be performed continuously, at each individual detected event, or in asynchronous fashion at one to five second intervals in various embodiments.

Figure 8:
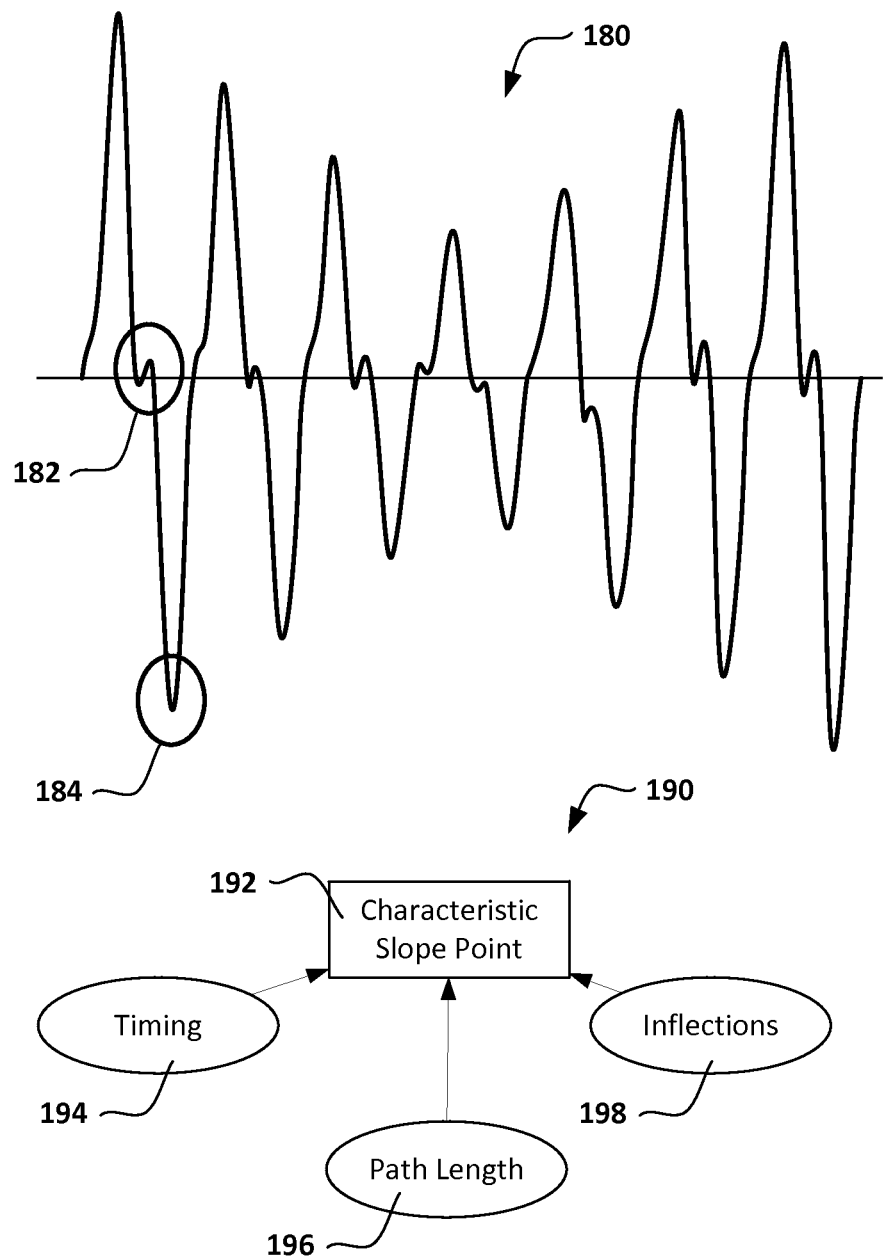
FIG. 8 demonstrates various factors which can be used to identify characteristic slope points.

A time interval is selected for analysis as noted at 132. The time interval may be in the range of 750 milliseconds to 3000 milliseconds, or longer or shorter. This time interval will be used to analyze the cardiac signal. Slope points are then identified, as noted at 134. In the example of FIG. 6, turning points 136 were used. In other examples, inflection points 138 (second derivative zeroes of the cardiac signal) may instead be used. In some examples, as illustrated in FIG. 8, below, not all slope points are included in this analysis at 134, with only "major" or "significant" slope points being assessed. Whether all or only some of the slope points are considered, these may be characterized as the "characteristic slope points" of the sensed signal.

Next it is determined whether the slope points are alternating, as shown at 140. Alternating, in this context, can mean that if a first slope point is of a first polarity, relative to a defined baseline, the next slope point should be of the opposite polarity. If the slope points do not alternate, the method ends as indicated at 160 without a finding of a TDP pattern.

If alternating slope points are found at block 140, the method continues by determining whether the slope points show equal spacing as shown at block 142. Any of several factors may be assessed in block 142. In some examples, intervals between pairs of positive polarity slope points are compared to intervals between pairs of negative polarity slope points, as noted at 144. In some examples, the set of intervals between pairs of positive polarity slope points are compared to one another to determine whether the positive polarity slope points are equally spaced one from another (and likewise the negative polarity slope points), as shown at 146. In some examples, the spacing between pairs of like-polarity slope points is compared to a boundary as well, as shown at 148, to determine whether the spacing is appropriate for supporting a finding of a TDP pattern.

If equal and appropriate spacing is not found at block 142, the method ends at 160 without a finding of a TDP pattern. Otherwise, a likely TDP is found, as shown at 150, leading to the application of acceleration factors, as shown at 152.

In some examples, the acceleration factor to apply includes an adjustment to an X/Y filter or NID tool, as shown at 154. An X/Y filter, in an illustrative example, calls for a certain quantity of detected events, X, out of a total quantity of detected events, Y, to meet arrhythmia parameters, such as demonstrating high rate or a morphology that suggests arrhythmia. Some examples use X/Y filters ranging from 8/12 out to 30/40, or less or more. An adjustment to an X/Y filter may include bumping up the value of X artificially. For example, an X/Y filter using a threshold of 18/24 may automatically have X increased by 4 if an acceleration factor is applied. In another example, an adjustment may include substituting (at least temporarily) a different X/Y threshold. For example, if the default is to use 30/40 as an X/Y filter, an acceleration factor may be applied by substituting 18/24 in place of the 30/40 threshold for a period of time (i.e., one minute to one hour).

An NID (number of intervals to detect) tool can be viewed as a subset of X/Y filters. Some examples may have a VT NID and a VF NID. The NID threshold may be reduced as an acceleration factor, or the variable which tracks NID may be bumped up as an acceleration factor. In some examples, a separate analytical track may be launched as an acceleration factor, for example, if separate VF NID and VT NID values are tracked by a device, a TDP NID may be activated and combines the VF and VT NID values into a single factor.

Another acceleration factor may include the suspension or disabling of a persistence factor, as shown at 156. In one example, persistence may be used to state that an X/Y filter or NID tool condition is required to persist for a period of time or a quantity of detections before an arrhythmia will be declared. U.S. Pat. No. 8,160,697, titled METHOD FOR ADAPTING CHARGE INITIATION FOR AN IMPLANTABLE CARDIOVERTER-DEFIBRILLATOR, the disclosure of which is incorporated by reference, provides some examples of persistence. An acceleration factor may undo the persistence requirement or set the persistence requirement to zero, for example.

Another illustrative acceleration factor can include simply declaring a VF has been detected, as shown at 158. This acceleration factor 158 would bypass other arrhythmia discrimination tools and goes directly to the declaration of treatable arrhythmia. In some examples, the declaration of VF at 158 would still be tempered by requiring that reconfirmation of the arrhythmia take place prior to therapy delivery, since it is typical for implantable therapy systems to require some period of time (typically 5-15 seconds) to prepare for high power defibrillation therapy to be delivered. During such preparations, the cardiac signal would continue to be analyzed to ensure that a treatable arrhythmia persists until therapy is delivered.

Once the acceleration factors are applied, the method can end at 160.

FIG. 8 demonstrates various illustrative factors which can be used to identify characteristic slope points. The upper part 180 of FIG. 8 shows an illustrative cardiac signal. There are multiple turning points in each cycle, including a notch at 182 and a peak at 184. It may be desirable for purposes of the methods shown in FIGS. 6-7 to avoid counting the notch 182. Therefore certain factors may be observed, as shown in the lower part of the FIG. 190. For example, characteristic slope points 192 may be counted, rather than all slope points. Some slope points may be excluded based on timing, as indicated at 194. For example, two slope points that are very close together may be ignored as one or both may suggest a notch, rather than a true peak. In another example, the path length between two turning points may be assessed, as shown at 196. A very short path length between two turning points can again suggest a notch. In another example, a method may determine whether there is a larger maximum or minimum within a selected period of time of a given turning point, to ensure that the actual peak rather than a notch or small peak is identified.

In another example, inflections are used as the slope points, as shown at 198. To ensure that only desired inflections are identified, it may be useful to check one or both of timing and path length, as well as whether a turning point appears between two inflection points. If the timing or path length are too short, or if there is no turning point between two inflections, then the inflection may be ignored as an insignificant inflection.

Figure 9:
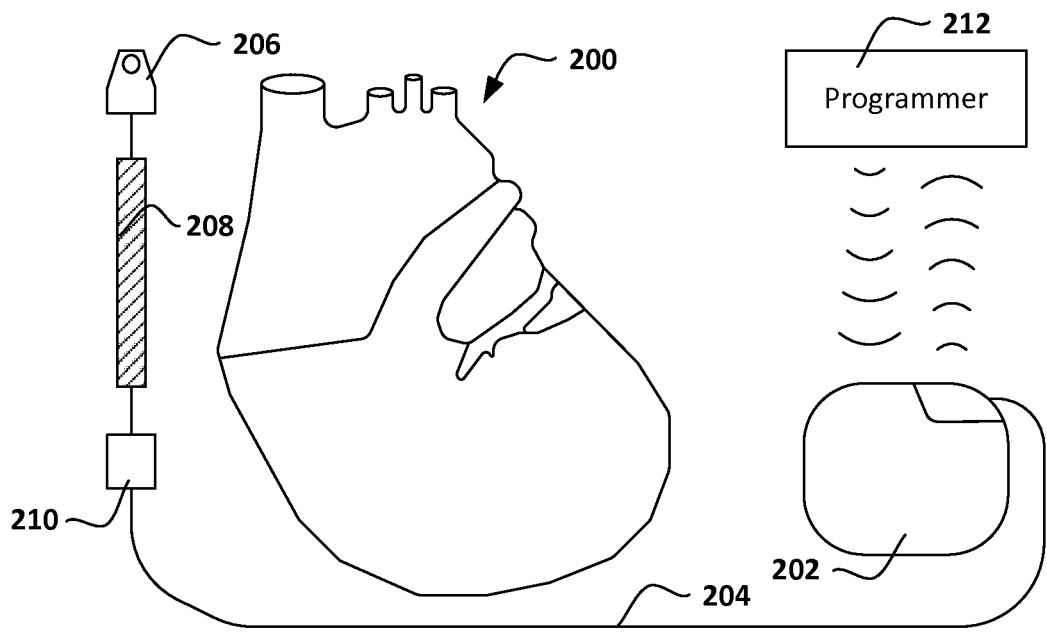
FIGS. 9-10 show illustrative subcutaneous-only and transvenous, intracardiac rhythm management systems, respectively.
Figure 10:
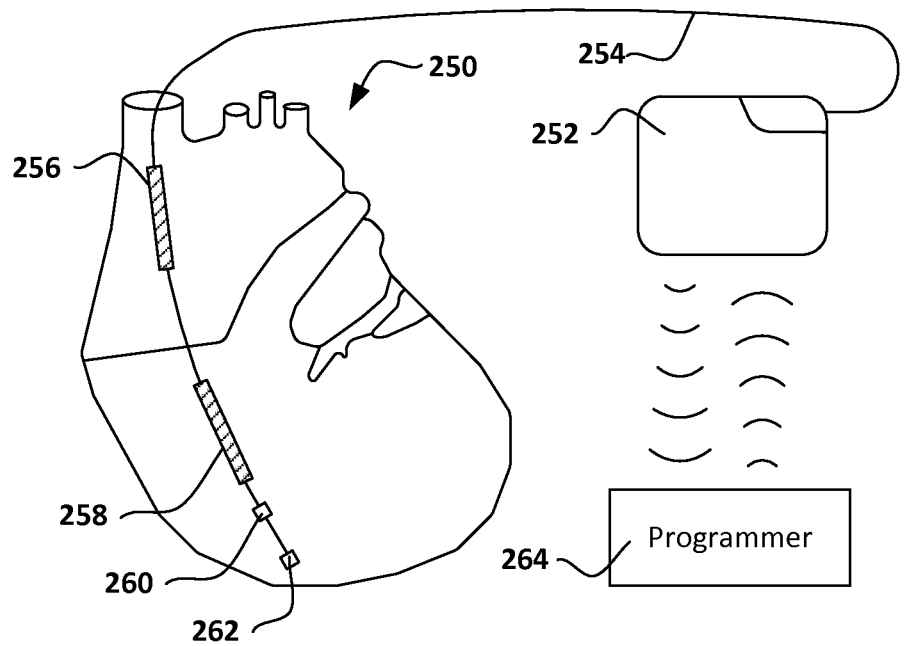

FIGS. 9-10 show illustrative subcutaneous-only and transvenous, intracardiac rhythm management systems, respectively. The present invention may find application in a subcutaneous-only system as illustrated in FIG. 9, or in a transvenous system as shown in FIG. 10. Alternatives may include systems having multiple subcutaneous and transvenous elements, epicardial systems, or fully intravenous or intracardiac systems.

The illustrative system shown in FIG. 9 is shown relative to a heart 200 and is intended to convey a subcutaneous implant that would take place over the ribs of the patient and beneath the patient's skin. A canister 202 is implanted near the left axilla, with lateral, anterior, or posterior positions being possible. A lead 204 couples the canister 202 to electrodes 206, 208 and 210, which are illustrated as implanted along the sternum of the patient, typically to the left or right thereof. The system in FIG. 9 may include an external programmer 212 configured for communication with the implant 202.

The system in FIG. 10 is a transvenous system, illustratively shown relative to the heart 250 again with the patient's ribs omitted for clarity. The canister 252 is in a high pectoral position, with the lead 254 accessing the vasculature and entering the heart. The lead 254 may include a superior vena cava coil electrode 256, a right ventricular coil electrode 258, and one or two ventricular sense/pace electrodes 260, 262. Again a programmer is shown at 264 and configured for communication with the implanted system. The system may further include a left ventricular lead (not shown).

Communication for either of the systems in FIG. 9 or 10 may be inductive, RF or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

The canisters in FIGS. 9 and 10 contain operational circuitry for the implantable system. The operational circuitry may include a controller and any suitable analog and/or digital circuits needed for signal processing, memory storage and generation of high-power electrical, low-power electrical and/or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes. The leads and external shell for the canisters can be manufactured with various materials suitable for implantation, such as those widely known, along with coatings for such materials, throughout the art. For example, the canisters can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes can be formed of suitable materials as well, such as silver, gold, titanium or stainless steel such as MP35N stainless steel alloy, or other materials.

The location of system implant may vary. For example, the system shown is a subcutaneous-only system located on the anterior and lateral chest between the skin and ribcage of the patient. Other subcutaneous only systems (including systems without a lead 204, with multiple leads 204, or an array in place of lead 204) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular. A subcutaneous-only defibrillator may also be used in combination with a fully intracardiac device such as a seed pacer, for example, the Nanostim™ leadless pacemaker or Micra™ transcatheter pacing system.

Other systems may include one or more transvenous leads or epicardial leads/electrodes, and may use different canister implant locations, such as placing the canister in a higher pectoral position closer to the clavicle for closer venous access, or abdominal placement. Illustrative transvenous systems include single chamber, dual chamber and biventricular systems. A fully intravenous system has also been proposed. Additional or other coatings or materials than those noted above may be used, particularly for epicardial, transvenous or intravenous systems, leads and canisters.

Various alternatives and details for these designs, materials and implantation approaches are known to those skilled in the art. Commercially available systems in which the above methods can be performed or which may be configured to perform such methods are known including the Boston Scientific Teligen™ ICD and S-ICD™ System, Medtronic Concerto™ and Virtuoso™ systems, and St. Jude Medical Promote™ RF and Current™ RF systems. Such platforms include numerous examples and alternatives for the operational circuitry, battery, canister, lead, and other system elements.

Figure 11:
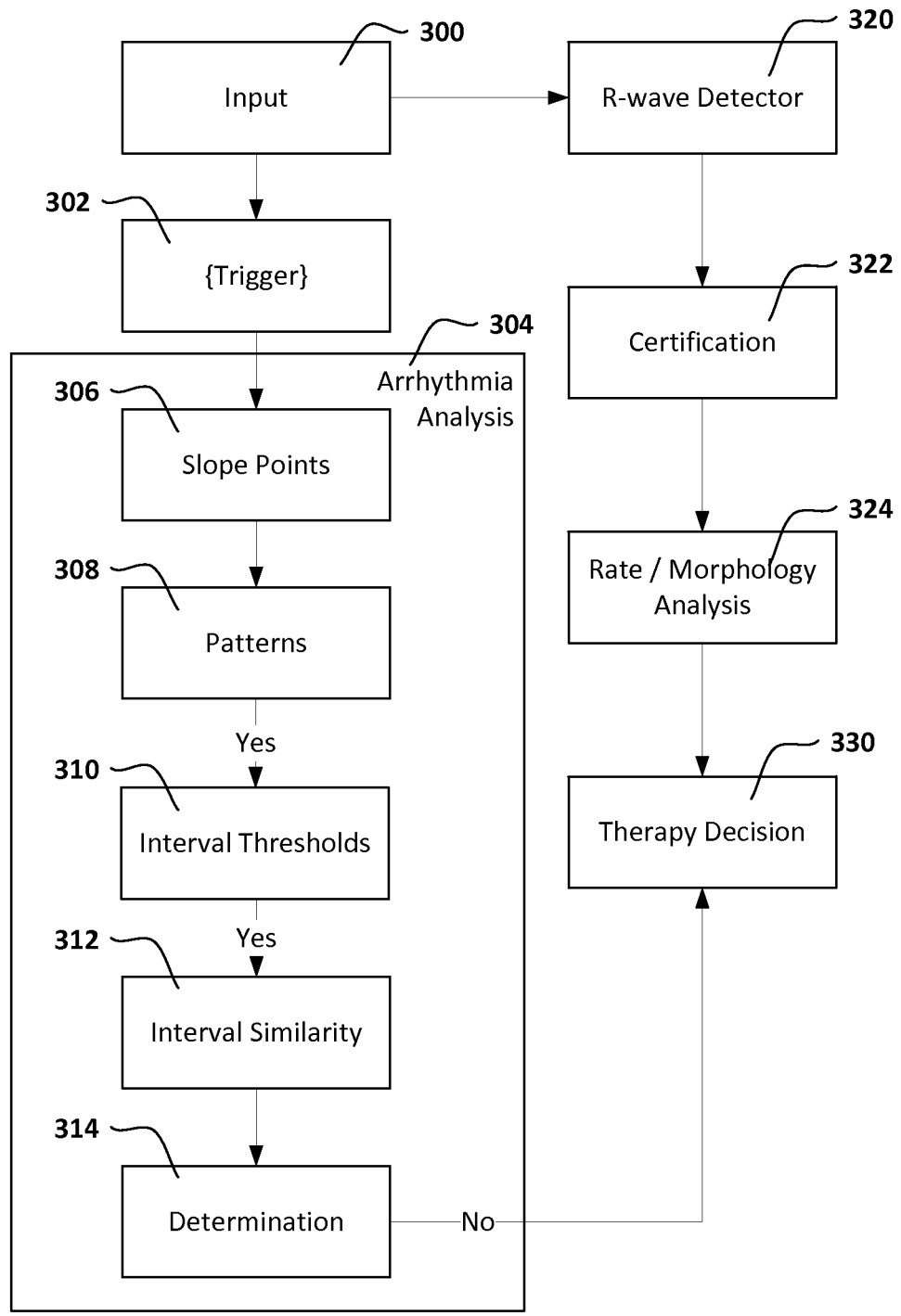
FIG. 11 is a block diagram for another illustrative approach.

FIG. 11 shows another illustrative approach. Beginning at 300, an input from associated device electrodes is taken. An optional trigger 302 can be included to start the arrhythmia analysis 304. As noted above, the trigger 302 may be omitted. In some embodiments, trigger 302 may look for two or three closely coupled detected events, or it may look for an interval pattern based on ordinary detection such as a long-short-short pattern or a short-short-long pattern.

Once started (trigger or no), the arrhythmia analysis 304 includes identification of slope points 306, checking for patterns 308, checking interval thresholds 310, and checking for interval similarity 312. The slope points sought at 306 may be local inflection points or local amplitude peaks. The patterns sought at 308 can include an alternating pattern of ABABAB around the signal baseline, where the signal baseline can be set via the input 300.

Interval thresholds at 310 can include high and low thresholds to avoid detecting noise or even the rapid succession of turning points observed at certain points of the normal cardiac cycle, and high thresholds to avoid operating too actively when slow rates are occurring. For example, the interval thresholds 310 may look at the intervals between successive slope points, requiring the intervals be greater than 50 or 100 milliseconds to avoid allowing a supraventricular tachycardia, such as an exercise induced rhythm, which would have a set of turning points around the QRS complex which occurs quickly, from being misidentified as a treatable arrhythmia. The low threshold may also prevent misidentification of noise. The high threshold, in the range of 400-600 milliseconds, is intended to avoid marking a biphasic normal sinus rhythm, or other slow rhythm, as an arrhythmia.

Next, interval similarity is assessed, as shown at 312. Here, the intervals between alternating slope points (which will have already been checked for their alternating polarity pattern at 308) are measured and compared to one another. As noted in FIG. 7, interval similarity can place the intervals into two sets, one for the positive characteristic slope points and one for the negative characteristic slope points. If using inflection points, the positive characteristic slope points can be inflection points occurring during an upward slope of the signal—that is, while second derivative zeroes while the first derivative is positive—and the negative characteristic slope points can be inflection points occurring during a downward slope of the signal. The sets may be internally analyzed for self-similarity or tight groups, and also compared to one another using such measures as the median, average, maxima or minima.

Finally, a determination is made at 314 as to whether the arrhythmia analysis 304 yields a positive result. If so, then the therapy decision 330 is modified accordingly. For example, the therapy decision 330 may adjust a stored value for an NID or X-out-of-Y filter, or may automatically declare an arrhythmia.

On an alternate track, FIG. 11 also shows a more conventional approach in which an R-wave detection 320 provides detected events for certification 322. Certification may include the identification and elimination of noise and overdetection. Next, rate/morphology analysis can be performed on the certified events, as shown at 324, leading to a conventional therapy decision 330 which may use, for example and as noted above, one or more NID counters or X-out-of-Y filters.

VARIOUS NOTES & EXAMPLES

A first non-limiting example takes the form of an implantable medical device comprising electrodes for capturing cardiac signals, the device comprising input means for receiving a signal from the electrodes and establishing a baseline for the received signal; and arrhythmia analysis means configured to identify an arrhythmia pattern in the received signal, wherein the arrhythmia analysis means includes slope point means for identifying characteristic slope points in the received signal; pattern means for determining whether the characteristic slope points form a pattern of alternating polarity about the baseline; interval threshold means for determining whether intervals defined by the characteristic slope points meet threshold criteria; interval similarity means for determining whether intervals between alternating ones of the characteristic slope points meet similarity criteria; and determining means for determining that an arrhythmia pattern exists if: the pattern means finds a pattern of alternating polarity about the baseline; the interval threshold means finds the threshold criteria are met; and the interval similarity means finds that the intervals between alternating ones of the characteristic slope points meet the similarity criteria. An example of input means is shown at 300 and associated description relative to FIG. 11. An example of arrhythmia analysis means is illustrated at 304 and associated description relative to FIG. 11, including slope point means 306, pattern means 308, interval threshold means 310, interval similarity means 312, and determining means 314.

A second non-limiting example takes the form of an implantable medical device as in the first non-limiting example, further comprising decision means for deciding whether the device ought to provide a therapy, wherein the arrhythmia analysis means is configured to issue an acceleration command to the decision means if an arrhythmia pattern exists. An example of therapy decision means is illustrated at 330 associated description relative to FIG. 11.

A third non-limiting example takes the form of an implantable medical device as in the second non-limiting example, wherein the decision means is configured to decide that the device ought to provide therapy more quickly than it otherwise would if an acceleration command is received, wherein the decision means includes an NID filter or X-out-of-Y filter, and the acceleration command causes the decision means to add to the NID or increase X, respectively. A fourth non-limiting example takes the form of an implantable medical device as in the second non-limiting example, wherein the acceleration command causes the decision means to automatically declare a treatable arrhythmia.

A fifth non-limiting example takes the form of an implantable medical device as in any of the first four non-limiting examples, further comprising event detection means for detecting cardiac cycles. An example of event decision means is shown at 320, an R-wave detector, in FIG. 11 and associated description.

A sixth non-limiting example takes the form of an implantable medical device as in the fifth non-limiting example, further comprising trigger means for activating the arrhythmia analysis means if a detection trigger is identified. A seventh non-limiting example takes the form of an implantable medical device as in the sixth non-limiting example, wherein the detection trigger is identified by finding two detected cardiac cycles occurring in less than a threshold period of time. An eighth non-limiting example takes the form of an implantable medical device as in the sixth non-limiting example, wherein the detection trigger is identified by finding three detected cardiac cycles occurring in less than a threshold period of time. A ninth non-limiting example takes the form of an implantable medical device as in the sixth non-limiting example, wherein the detection trigger is identified by finding a pattern of intervals between detected cardiac cycles in which a long interval follows or precedes two short intervals, the long and short intervals being defined by respective long and short interval thresholds.

A tenth non-limiting example takes the form of an implantable medical device as in any of the first nine non-limiting examples, wherein the threshold criteria require that intervals between alternating characteristic slope points are greater than a minimum threshold and less than a maximum threshold. An eleventh non-limiting example takes the form of an implantable medical device as in any of the first ten non-limiting examples, wherein the characteristic slope points are local maxima and minima of the received signal. A twelfth non-limiting example takes the form of an implantable medical device as in any of the first ten non-limiting examples, wherein the characteristic slope points are local inflection points of the received signal.

A thirteenth non-limiting example takes the form of an implantable medical device as in any of the first twelve non-limiting example, wherein the characteristic slope points include at least some candidate slope points by analyzing path length between a given slope point and a characteristic slope point. A fourteenth non-limiting example takes the form of an implantable medical device as in any of the first thirteen non-limiting example, wherein the interval similarity means is operable by identifying a set of intervals between positive characteristic slope points and a set of intervals between negative characteristic slope points, and comparing the two sets of intervals. A fifteenth non-limiting example takes the form of an implantable medical device as in the fourteenth non-limiting example, wherein comparing the two sets of intervals includes comparing at least one of the average, median, maximum and minimum in each of the sets of intervals.

A sixteenth non-limiting example takes the form of a method of accelerating identification of an arrhythmia in an implantable cardiac treatment system comprising: applying a detection threshold to a sensed signal to detect cardiac events; identifying a plurality of closely coupled detected cardiac events; setting a window of analysis preceding at least one of the closely coupled detected cardiac events; identifying characteristic slope points in the sensed signal in the window of analysis and labeling the slope points as at least ABAB; determining whether an arrhythmia pattern exists in which: the slope points illustrate alternating polarity around a baseline such that the slope points labeled "A" are of one polarity and the slope points labeled "B" are of an opposite polarity; intervals between slope points labeled A are similar to intervals between slope points labeled B; and intervals between slope points labeled A fall between a minimum interval threshold and a maximum interval threshold; and, if an arrhythmia pattern exists, applying an acceleration condition to an arrhythmia detection method.

A seventeenth non-limiting example takes the form of a method as in the sixteenth non-limiting example, wherein the plurality of closely coupled detected events comprises at least two detected events. An eighteenth non-limiting example takes the form of a method as in the sixteenth non-limiting example, wherein the plurality of closely coupled detected events comprises at least three detected events.

A nineteenth non-limiting example takes the form of a method as in any of the sixteenth through eighteenth non-limiting examples, wherein the window of analysis has a duration in the range of 1-3 seconds.

A twentieth non-limiting example takes the form of a method as in any of the sixteenth through nineteenth non-limiting examples, wherein the step of identifying characteristic slope points in the sensed signal in the window of analysis comprises identifying all turning points in the sensed signal in the window of analysis. A twenty-first non-limiting example takes the form of a method as in the twentieth non-limiting example, wherein the step of identifying characteristic slope points in the sensed signal in the window of analysis comprises identifying only major turning points. A twenty-second non-limiting example takes the form of a method as in the twenty-first non-limiting example, wherein the step of identifying only major turning points comprises identifying only those turning points which are separated by at least a threshold interval. A twenty-third non-limiting example takes the form of a method as in the twenty-first non-limiting example, wherein the step of identifying only major turning points comprises identifying only those turning points which are separated by at least a threshold path length. A twenty-fourth non-limiting example takes the form of a method as in the twenty-first non-limiting example, wherein the step of identifying only major turning points comprises identifying only turning points separated by at least two inflection points.

A twenty-fifth non-limiting example takes the form of a method as in any of the sixteenth through nineteenth non-limiting examples, wherein the step of identifying characteristic slope points in the sensed signal in the window of analysis comprises identifying inflection points. A twenty-sixth non-limiting example takes the form of a method as in the twenty-fifth non-limiting example, wherein the step of identifying characteristic slope points in the sensed signal in the window of analysis comprises identifying only those inflection points having a turning point therebetween. A twenty-seventh non-limiting example takes the form of a method as in the twenty-fifth non-limiting example, wherein the step of identifying characteristic slope points in the sensed signal in the window of analysis comprises identifying only those inflection points having a minimum path length therebetween.

A twenty-eighth non-limiting example takes the form of a method as in any of the sixteenth through twenty-seventh non-limiting examples, wherein the minimum interval threshold is selected to prevent noise from causing a positive identification of arrhythmia, and the maximum interval threshold is selected to prevent a non-treatable cardiac signal from causing a positive identification of arrhythmia. A twenty-ninth non-limiting example takes the form of a method as in any of the sixteenth through twenty-eighth non-limiting examples, wherein the arrhythmia detection method comprises the use of an X/Y filter and the acceleration condition, when applied, does at least one of the following: increase X; or reduce a relative X/Y threshold. A thirtieth non-limiting example takes the form of a method as in any of the sixteenth through twenty-eighth non-limiting examples, wherein the arrhythmia detection method comprises the use of several NID factors specific to different therapy regimens, and the acceleration condition only affects an NID factor specific to a defibrillation shock therapy regimen. A thirty-first non-limiting example takes the form of a method as in any of the sixteenth through thirtieth non-limiting examples, wherein the arrhythmia detection method comprises the use of a persistence factor which requires that an arrhythmia persist for a period of time or a quantity of analytical iterations, and the acceleration condition reduces or eliminates the persistence factor.

A thirty-second non-limiting example takes the form of an implantable cardiac device comprising operational circuitry contained in a housing and configured for coupling to a plurality of implantable electrodes, in which the operational circuitry is configured to perform a method as in any of the sixteenth to thirty-first non-limiting examples.

A thirty-third non-limiting example takes the form of an implantable cardiac device comprising operational circuitry contained in a housing and configured for coupling to a plurality of implantable electrodes, in which the operational circuitry is configured to apply a detection threshold to a sensed signal taken from the plurality of implantable electrodes when coupled thereto in order to detect cardiac events; identify a plurality of closely coupled detected cardiac events; set a window of analysis preceding at least one of the closely coupled detected cardiac events; identify characteristic slope points in the sensed signal in the window of analysis and label the slope points as at least ABAB; determine whether an arrhythmia pattern exists in which: the slope points illustrate alternating polarity around a baseline such that the slope points labeled "A" are of one polarity and the slope points labeled "B" are of an opposite polarity; intervals between slope points labeled A are similar to intervals between slope points labeled B; and intervals between slope points labeled A fall between a minimum interval threshold and a maximum interval threshold; if an arrhythmia pattern exists, apply an acceleration condition to an arrhythmia detection method.

A thirty-fourth non-limiting example takes the form of an implantable cardiac device as in the thirty-third non-limiting example, wherein the operational circuitry is configured such that the arrhythmia detection method comprises the use of an X/Y filter and the acceleration condition, when applied, does at least one of the following: increase X; or reduce a relative X/Y threshold.

A thirty-fifth non-limiting example takes the form of an implantable cardiac device as in the thirty-third non-limiting example, wherein the operational circuitry is configured such that the arrhythmia detection method comprises the use of several NID factors specific to different therapy regimens, and the acceleration condition only affects an NID factor specific to a defibrillation shock therapy regimen.

A thirty-sixth non-limiting example takes the form of an implantable cardiac device as in any of the thirty-third to thirty-fifth non-limiting examples, wherein the operational circuitry is configured such that the arrhythmia detection method comprises the use of a persistence factor which requires that an arrhythmia persist for a period of time or a quantity of analytical iterations, and the acceleration condition reduces or eliminates the persistence factor.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of accelerating identification of an arrhythmia in an implantable cardiac treatment system, the implantable cardiac treatment system comprising at least two electrodes for sensing cardiac activity coupled, electrically, to operational circuitry for analyzing sensed cardiac activity, the method comprising the operational circuitry:
   applying a detection threshold to a sensed cardiac activity signal to detect cardiac events;
   identifying a plurality of closely coupled detected cardiac events, wherein the plurality of closely coupled detected includes at least two detected cardiac events occurring within a predetermined coupling time interval;
   setting a window of analysis preceding at least one of the closely coupled detected cardiac events;
   identifying characteristic slope points in the sensed signal in the window of analysis and labeling the slope points as at least ABAB;
   determining whether an arrhythmia pattern exists in which:
      the slope points illustrate alternating polarity around a baseline such that the slope points labeled "A" are of one polarity and the slope points labeled "B" are of an opposite polarity;
      intervals between slope points labeled A are similar to intervals between slope points labeled B; and
      intervals between slope points labeled A fall between a minimum interval threshold and a maximum interval threshold;
   if an arrhythmia pattern exists, applying an acceleration condition to an arrhythmia detection method to cause operational circuitry of the implantable cardiac treatment system to reach a declaration of a treatable arrhythmia and deliver a therapy via at least one of the electrodes to terminate the arrhythmia.

2. The method of claim 1 wherein the plurality of closely coupled detected events comprises at least two detected events.

3. The method of claim 1 wherein the plurality of closely coupled detected events comprises at least three detected events.

4. The method of claim 1 wherein the window of analysis has a duration in the range of 1-3 seconds.

5. The method of claim 1 wherein the step of identifying characteristic slope points in the sensed signal in the window of analysis comprises identifying all turning points in the sensed signal in the window of analysis.

6. The method of claim 1 wherein the step of identifying characteristic slope points in the sensed signal in the window of analysis comprises identifying only major turning points, the major turning points being turning points which are separated by at least a threshold turning point interval.

7. The method of claim 6 wherein the step of identifying only major turning points comprises identifying only those turning points which are separated by at least a threshold path length.

8. The method of claim 6 wherein the step of identifying only major turning points comprises identifying only turning points separated by at least two inflection points.

9. The method of claim 1 wherein the step of identifying characteristic slope points in the sensed signal in the window of analysis comprises identifying inflection points including only inflection points having a turning point therebetween.

10. The method of claim 1 wherein the step of identifying characteristic slope points in the sensed signal in the window of analysis comprises identifying inflection points including only inflection points having a minimum path length therebetween.

11. The method of claim 1 wherein the minimum interval threshold is selected to prevent noise from causing a positive identification of arrhythmia, and the maximum interval threshold is selected to prevent a non-treatable cardiac signal from causing a positive identification of arrhythmia.

12. The method of claim 1 wherein the arrhythmia detection method comprises the use of an X/Y filter and the acceleration condition, when applied, does at least one of the following:
increase X; or
reduce a relative X/Y threshold.

13. The method of claim 1 wherein the arrhythmia detection method comprises the use of several number of intervals to detect (NID) factors specific to different therapy regimens, and the acceleration condition only affects an NID factor specific to a defibrillation shock therapy regimen.

14. The method of claim 1 wherein the arrhythmia detection method comprises the use of a persistence factor which requires that an arrhythmia persist for a period of time or a quantity of analytical iterations, and the acceleration condition reduces or eliminates the persistence factor.

15. A method as in claim 1 wherein the predetermined coupling time interval is 300 milliseconds.

16. An implantable cardiac device comprising operational circuitry contained in a housing and configured for coupling to a plurality of implantable electrodes, the operational circuitry being configured to perform the following:
apply a detection threshold to a sensed signal taken from the plurality of implantable electrodes when coupled thereto in order to detect cardiac events;
identify a plurality of closely coupled detected cardiac events, wherein the plurality of closely coupled detected includes at least two detected cardiac events occurring within a predetermined coupling time interval;
set a window of analysis preceding at least one of the closely coupled detected cardiac events;
identify characteristic slope points in the sensed signal in the window of analysis and label the slope points as at least ABAB;
determine whether an arrhythmia pattern exists in which:
the slope points illustrate alternating polarity around a baseline such that the slope points labeled "A" are of one polarity and the slope points labeled "B" are of an opposite polarity;
intervals between slope points labeled A are similar to intervals between slope points labeled B; and
intervals between slope points labeled A fall between a minimum interval threshold and a maximum interval threshold;
if an arrhythmia pattern exists, apply an acceleration condition to an arrhythmia detection method to cause operational circuitry of the implantable cardiac device to reach a declaration of a treatable arrhythmia and deliver a therapy via at least one of the electrodes to terminate the arrhythmia.

17. An implantable cardiac device as in claim 16 wherein the operational circuitry is configured such that the arrhythmia detection method comprises the use of an X/Y filter and the acceleration condition, when applied, does at least one of the following:
increase X; or
reduce a relative X/Y threshold.

18. An implantable cardiac device as in claim 16 wherein the operational circuitry is configured such that the arrhythmia detection method comprises the use of several number of intervals to detect (NID) factors specific to different therapy regimens, and the acceleration condition only affects an NID factor specific to a defibrillation shock therapy regimen.

19. An implantable cardiac device as in claim 16 wherein the operational circuitry is configured such that the arrhythmia detection method comprises the use of a persistence factor which requires that an arrhythmia persist for a period of time or a quantity of analytical iterations, and the acceleration condition reduces or eliminates the persistence factor.

20. An implantable cardiac device as in claim 16 wherein the operational circuitry is configured such that the predetermined coupling time interval is 300 milliseconds.

* * * * *